United States Patent
Groux et al.

(10) Patent No.: US 12,410,472 B2
(45) Date of Patent: Sep. 9, 2025

(54) METHOD FOR EVALUATING THE EYE IRRITATION POTENTIAL OF CHEMICALS

(71) Applicant: IMMUNOSEARCH, Le Plan de Grasse (FR)

(72) Inventors: Hervé Groux, Le Rouret (FR); Françoise Cottrez, Le Rouret (FR); Nathalie Alepee, Livry Gargan (FR); Virginie Leblanc, Cachan (FR)

(73) Assignee: IMMUNOSEARCH, Le Plan de Grasse (FR)

( * ) Notice: Subject to any disclaimer, the term of this patent is extended or adjusted under 35 U.S.C. 154(b) by 1260 days.

(21) Appl. No.: 16/334,269

(22) PCT Filed: Sep. 19, 2017

(86) PCT No.: PCT/EP2017/073675
§ 371 (c)(1),
(2) Date: Mar. 18, 2019

(87) PCT Pub. No.: WO2018/050927
PCT Pub. Date: Mar. 22, 2018

(65) Prior Publication Data
US 2019/0300952 A1      Oct. 3, 2019

(30) Foreign Application Priority Data
Sep. 19, 2016  (FR) ..................................... 1658746

(51) Int. Cl.
| | | |
|---|---|---|
| *C12Q 1/68* | (2018.01) | |
| *C12Q 1/02* | (2006.01) | |
| *C12Q 1/6876* | (2018.01) | |
| *C12Q 1/6883* | (2018.01) | |

(52) U.S. Cl.
CPC ............ *C12Q 1/6876* (2013.01); *C12Q 1/02* (2013.01); *C12Q 1/6883* (2013.01); *C12Q 2531/113* (2013.01); *C12Q 2600/106* (2013.01); *C12Q 2600/142* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,854,033 A | 12/1998 | Lizardi |

FOREIGN PATENT DOCUMENTS

| | | |
|---|---|---|
| CA | 2318641 A1 | 7/1999 |
| FR | 2957090 A1 | 9/2011 |

OTHER PUBLICATIONS

Orita et al (Investigative Ophthalmology & Visual Science, 2010, vol. 51, No. 11, pp. 5556-5560) (Year: 2010).*
Mukwaya et al (Scientific Reports, 6: 32137, Aug. 26, 2016, pp. 1-15). (Year: 2016).*
Barany, "Genetic Disease Detection and DNA Amplification Using Cloned Thermostable Ligase," Proc. Natl. Acad. Sci. USA, vol. 88, Jan. 1991, pp. 189-193.
French Search Report dated Mar. 28, 2017, for French Application No. 1658746.
Guatelli et al., "Isothermal, In Vitro Amplification of Nucleic Acids by A Multienzyme Reaction Modeled After Retroviral Replication", Proc. Natl. Acad. Sci. USA, vol. 87, Mar. 1990, pp. 1874-1878.
International Search Report dated Oct. 30, 2017, for International Application No. PCT/EP2017/073675, with English translation.
Khoh-Reiter et al., "Evaluation of The Cytotoxic Effects of Ophthalmic Solutions Containing Benzalkonium Chloride On Corneal Epithelium Using an Organotypic 3-D Model", BMC Ophthalmology, vol. 9, No. 1, Jul. 28, 2009, pp. 5-11.
Kwoh et al., "Transcription-based Amplification System and Detection of Amplified Human Immunodeficiency Virus Type 1 With A Bead-based Sandwich Hybridization Format", Proc. Natl. Acad. Sci. USA, vol. 86, Feb. 1989, pp. 1173-1177.
Lizardi et al., "Exponential Amplification of Recombinant—RNA Hybridization Probes", Biol/Technology, vol. 6, Oct. 1988, pp. 1197-1202, 7 pages total.
Meloni et al., "Occludin Gene Expression as an Early in Vitro Sign for Mild Eye Irritation Assessment", Toxicology in Vitro, vol. 24, No. 1, Sep. 1, 2009, pp. 276-285.
Rönkkö et al., "Human Corneal Cell Culture Models for Drug Toxicity Studies", Drug Deliv. and Transl. Res., vol. 6, No. 6, Sep. 9, 2016, pp. 660-675.
Yamamoto et al., "Establishment of A New Immortalized Human Corneal Epithelial Cell Line (iHCE-NY1) For Use in Evaluating Eye Irritancy by in Vitro Test Methods", In Vitro Cell. Dev. Biol.—Animal, vol. 52, No. 7, Apr. 29, 2016, pp. 742-748.

* cited by examiner

*Primary Examiner* — Celine X Qian
(74) *Attorney, Agent, or Firm* — Birch, Stewart, Kolasch & Birch, LLP

(57) ABSTRACT

The present invention concerns an in vitro test for detecting the irritant potential of chemicals combining a corneal cell model with a selection of predictive and qualitative molecular markers to classify compounds into 3 categories, namely irreversible eye damage 21 days after application (category 1), reversible eye damage 21 days after application (category 2) and no irritation (no category). The inventors have thus demonstrated that the response following the action of an irritant substance occurs directly on an in vitro reconstructed corneal epithelium, and that the degree of irritation and the qualification of this irritation of a molecule may be determined by the use of specific biomarkers of eye irritation.

4 Claims, 2 Drawing Sheets

METHOD FOR EVALUATING THE EYE IRRITATION POTENTIAL OF CHEMICALS

Figure 1:
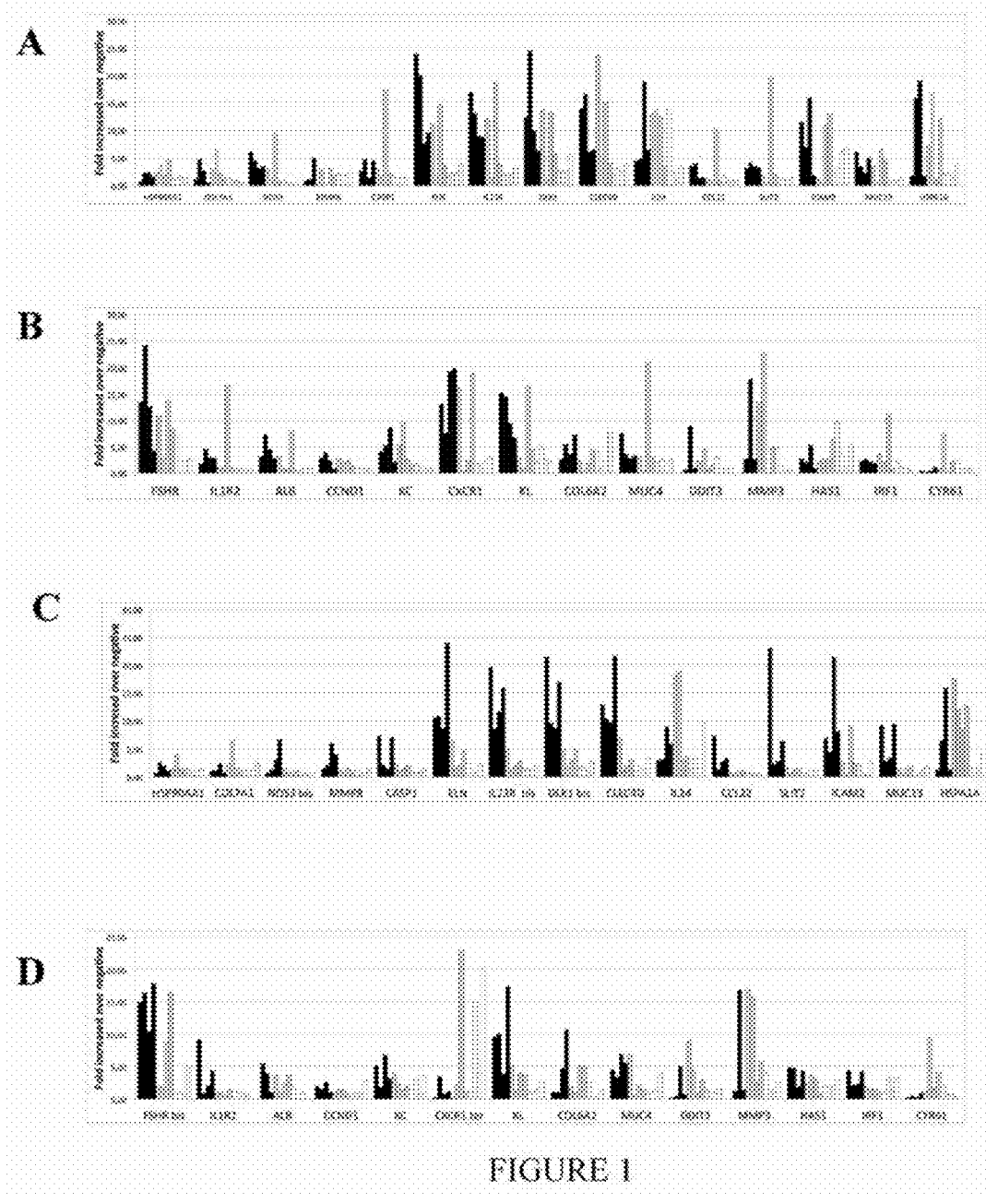

The present invention concerns a method for evaluating and categorizing the eye irritation potential of chemicals.

To assess the safety of chemicals in terms of the eye, there is the Draize test, an invasive toxicological test based on an animal testing protocol developed in 1944 by John H. Draize and Jacob M. Spines, toxicologists working at the Food and Drug Administration (FDA). The test consists of testing a product in the eye of an animal to assess its ocular safety.

In practice, it consists of applying 0.1 milliliter or 0.1 gram of a substance to the eye of a conscious animal, often a rabbit, for one to twenty-four hours. The animal is then monitored for a period of up to 21 days for the possible appearance of corneal opacity, conjunctivitis, edema, or secretions.

The use of animals in the laboratory for the Draize test is strongly opposed by animal welfare advocates. Within the European Union, animal testing is regulated by Directive 2010/63, which encourages the development of alternative testing methods.

Chemicals are classified according to a globalized system implemented by the United Nations known as the United Nations Globally Harmonized System, and with regard to eye irritation properties products are classified into several categories. Category 1 concerns products causing damage that has not reversed within 21 days, category 2A concerns products that cause eye irritation that is reversible within 21 days and category 2B concerns products that cause mild eye irritation that is reversible within 21 days. Non-irritating products are not classified. European legislation combines categories 2A and 2B into a single category 2 of reversible eye irritants.

There is also a procedure for estimating the ocular discomfort or irritant potential of a chemical such as a cosmetic product. This process comprises culturing an epidermis model in vitro, depositing the product to be studied on a cultured epidermis model, and quantifying the number of surviving living cells in order to assess ocular discomfort or irritant potential. Such a process, developed as a replacement for animal experimentation, has the disadvantage of being long and costly and not very discriminating. Moreover, this method is not a complete replacement method, as it does not reliably detect the full range of intermediate irritations.

Thus, it appears that there is a need for a test or method to replace the Draize test and to provide in particular a method to quickly differentiate and categorize compounds causing irreversible eye irritation at 21 days from those whose effects are reversible within 21 days.

The inventors of the present application therefore looked into the development of an in vitro test for detecting the irritant potential of chemicals combining a corneal cell model with a selection of predictive and qualitative molecular markers to classify compounds into 3 categories, namely irreversible eye damage 21 days after application (category 1), reversible eye damage 21 days after application (category 2) and no irritation (no category).

Surprisingly, the inventors have shown that the response to the action of an irritant substance occurs directly on an in vitro reconstructed corneal epithelium, and that the degree of irritation, and the qualification of this irritation, of a molecule can be determined by the use of specific biomarkers of eye irritation. It is particularly notable, and this is a surprising feature of the present method, that the molecular markers used have never been described or disclosed in relation to eye irritation.

The Inventors have demonstrated that an in vitro reconstructed corneal epithelium is a sufficient model to identify specific biomarkers of eye irritation in humans, and that these biomarkers can also be used to predict the degree of irritation and thus to predictively classify the products tested according to the 3 categories as indicated above.

Thus, the present invention relates to a method for evaluating the eye irritation potential of a test compound, comprising the steps of:
  a) bringing a test compound into contact with an in vitro reconstructed corneal sample;
  b) measuring the expression of at least one gene selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferably, the method according to the present invention may further comprise a step c) of determining an eye irritation index of a test compound.

Preferentially, the method also comprises a step d) of categorizing said compound as having an eye irritation potential based on the value of the eye irritation index obtained.

Preferably, the method according to the present invention is an in vitro method.

As used here, the term "in vitro reconstructed corneal sample" refers to a sample of corneal epithelial cells cultured in defined culture medium or any model using human squamous epithelial cells and having a morphology similar to the human cornea, such as the in vitro corneal models of the type marketed under the EpiOcular® brand.

More specifically, this "in vitro reconstructed corneal sample" is a sample comprising, or consisting of, immortalized corneal epithelial cells, grown in defined culture medium and arranged in a thin layer on a synthetic membrane at the water-air interface.

Preferably, said immortalized corneal epithelial cells are human cells.

In a particular embodiment, this "in vitro reconstructed corneal sample" is a SkinEthic® HCE sample marketed by Episkin (Lyon, France), which is a reconstructed corneal epithelium composed of human corneal keratinocytes, particularly cells transformed to be made immortal.

In a particular embodiment of the invention, the bringing into contact of the test compound in step a) is carried out with the test compound in solid form, for example in powder form.

In a particular embodiment of the invention, the bringing into contact of the test compound in step a) is carried out with the test compound in liquid form.

For the purposes of the present invention, measuring the expression of said at least one gene from step b) makes it possible to determine the expression level of said gene.

The test compound may be a compound of various nature, structure and origin, notably a biological compound, a chemical compound, a synthetic compound, etc.

The test compound may be any product that is in isolated form or mixed with other products. The test compound may be defined in terms of structure and/or composition or may be defined functionally. The test compound may, for example, be an isolated and structurally defined product, an isolated product of undetermined structure, a mixture of known and characterized products or a composition comprising one or more products. One or more compounds may thus be tested, in mixture or separately.

The present invention is particularly suitable for identifying a large number of compounds. This simple and efficient screening may be accomplished in a very short period of time. In particular, the methods described may be partially automated, thus allowing the efficient and simultaneous screening of many different compounds, either as a mixture or separately.

Preferably, in the method according to the present invention, the expression level of said gene is evaluated by measuring the expression level of the polypeptide encoded by said gene or a fragment thereof, or by measuring the expression level of the mRNA of said gene or a fragment thereof.

In a preferred embodiment, the expression of said at least one gene is carried out by analyzing the expression of mRNA transcripts or mRNA precursors, such as a native RNA, of said gene. This analysis may be performed by preparing the mRNA/cDNA of cells from a biological sample from a patient and hybridizing the mRNA/cDNA with a reference polynucleotide. Prepared mRNA/cDNA may be used in a hybridization or amplification assay that includes, but is not limited to, Southern and Northern assays, polymerase chain reaction (PCR) assays, such as quantitative PCR (TagMan) and the use of probe arrays such as GeneChip® DNA matrices (AFFYMETRIX).

Advantageously, the analysis of the expression of the level of transcribed mRNA of said at least one gene involves a nucleic acid amplification process, such as RT-PCR (experimental embodiment described in U.S. Pat. No. 4,683,202), the ligase chain reaction (BARANY, Proc. Natl. Acad. Sci. USA, vol. 88), p: 189-193, 1991), self-sustained sequence replication (GUATELLI et al., Proc. Natl. Acad. Acad. Sci. USA, vol. 87, p: 1874-1878, 1990), the transcriptional amplification system. (KWOH et al., Proc. Natl. Acad. Acad. Sci. USA, vol. 86, p. 1173-1177, 1989), "Q-Beta Replicase" (LIZARDI et al., Biol. Technology, vol. 6, p. 1197, 1988), rolling-circle replication (U.S. Pat. No. 5,854,033) or any other nucleic acid amplification method, followed by a step of detecting the amplified molecules by techniques well-known to the skilled person. These detection methods are particularly useful for detecting nucleic acid molecules in very small quantities.

Thus, according to a preferred embodiment, the method according to the present invention comprises an additional step of amplifying the mRNA or cDNA of said gene, the complementary sequence thereof or a fragment thereof.

As used here, amplification primers are defined as a pair of nucleic acid molecules that can be matched specifically to the respective 3' and 5' regions of a gene (positive and negative strands, or vice versa) and flank a short region of said gene. Generally, amplification primers have a length of 10 to 30 nucleotides and allow the amplification of a region of a length comprised between 50 and 200 nucleotides.

In another preferred embodiment, the measurement of the expression of said at least one gene is performed by measuring the expression level of the polypeptide encoded by said gene. Said analysis may be performed using an antibody (e.g., a radio-, chromophore-, fluorophore- or enzyme-labeled antibody), an antibody derivative (e.g., an antibody conjugated to a substrate or to a protein or a ligand of a protein of a ligand/protein pair (e.g., biotin-streptavidin)) or an antibody fragment (e.g., a single-chain antibody, a hypervariable domain of an isolated antibody, etc.) which specifically binds to the polypeptide encoded by said gene. These analyses may be carried out by many techniques familiar to the skilled person, techniques which include, but are not limited to, immunological tests based on the use of enzyme activity (enzyme immunoassay, EIA), immunological tests based on the use of radioactive isotopes (RIA), Western blot analysis and enzyme-linked immunosorbent assay (ELISA).

For the purposes of the present invention, "polypeptide" means a sequence comprising at least two amino acids, and the terms "polypeptide", "peptide" and "protein" may be used interchangeably.

"Fragment of mRNA or cDNA" means a sequence of at least 50 nucleic acids, by way of example of at least 100 or 150 nucleic acids, preferably of at least 200 nucleic acids, by way of example of at least 250 or 350 nucleic acids, and particularly preferably a polypeptide of at least 400 nucleic acids.

"Fragment of the polypeptide" means a sequence of at least 50 amino acids, by way of example of at least 100 or 150 amino acids, preferably of at least 200 amino acids, by way of example of at least 250 or 350 amino acids, and particularly preferably a polypeptide of at least 400 amino acids.

Preferentially, said method assesses the eye irritation potential of a test compound, wherein step b) comprises measuring the expression of at least two genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least three genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least four genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least five genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least six genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least seven genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least eight genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least nine genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least ten genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least eleven genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least twelve genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, wherein step b) comprises measuring the expression of at least thirteen genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61.

Preferentially, said method assesses the eye irritation potential of a test compound, particularly when the bringing into contact of the test compound in step a) is carried out with the test compound in liquid form, wherein step b) comprises measuring the expression of at least one gene selected from the group consisting of: HSP90AA1, CASP1, DLK1, CLEC4D, IL-24, SLIT2, HSPA1A, FSHR, IL-1R2 and CCND1.

Preferentially, said method assesses the eye irritation potential of a test compound, particularly when the bringing into contact of the test compound in step a) is carried out with the test compound in liquid form, wherein step b) comprises measuring the expression of at least two genes selected from the group consisting of: HSP90AA1, CASP1, DLK1, CLEC4D, IL-24, SLIT2, HSPA1A, FSHR, IL-1R2 and CCND1.

Preferentially, said method assesses the eye irritation potential of a test compound, particularly when the bringing into contact of the test compound in step a) is carried out with the test compound in liquid form, wherein step b) comprises measuring the expression of at least three genes selected from the group consisting of: HSP90AA1, CASP1, DLK1, CLEC4D, IL-24, SLIT2, HSPA1A, FSHR, IL-1R2 and CCND1.

Preferentially, said method assesses the eye irritation potential of a test compound, particularly when the bringing into contact of the test compound in step a) is carried out with the test compound in liquid form, wherein step b) comprises measuring the expression of at least four genes selected from the group consisting of: HSP90AA1, CASP1, DLK1, CLEC4D, IL-24, SLIT2, HSPA1A, FSHR, IL-1R2 and CCND1.

Preferentially, said method assesses the eye irritation potential of a test compound, particularly when the bringing into contact of the test compound in step a) is carried out with the test compound in liquid form, wherein step b) comprises measuring the expression of at least five genes selected from the group consisting of: HSP90AA1, CASP1, DLK1, CLEC4D, IL24, SLIT2, HSPA1A, FSHR, IL1R2 and CCND1.

Preferentially, said method assesses the eye irritation potential of a test compound, particularly when the bringing into contact of the test compound in step a) is carried out with the test compound in liquid form, wherein step b) comprises measuring the expression of at least six genes selected from the group consisting of: HSP90AA1, CASP1, DLK1, CLEC4D, IL24, SLIT2, HSPA1A, FSHR, IL1R2 and CCND1.

Preferentially, said method assesses the eye irritation potential of a test compound, particularly when the bringing into contact of the test compound in step a) is carried out with the test compound in liquid form, wherein step b) comprises measuring the expression of at least seven genes selected from the group consisting of: HSP90AA1, CASP1, DLK1, CLEC4D, IL-24, SLIT2, HSPA1A, FSHR, IL1R2 and CCND1.

Preferentially, said method assesses the eye irritation potential of a test compound, particularly when the bringing into contact of the test compound in step a) is carried out with the test compound in liquid form, wherein step b) comprises measuring the expression of at least eight genes selected from the group consisting of: HSP90AA1, CASP1, DLK1, CLEC4D, IL24, SLIT2, HSPA1A, FSHR, IL1R2 and CCND1.

Preferentially, said method assesses the eye irritation potential of a test compound, particularly when the bringing into contact of the test compound in step a) is carried out with the test compound in liquid form, wherein step b) comprises measuring the expression of at least nine genes selected from the group consisting of: HSP90AA1, CASP1, DLK1, CLEC4D, IL24, SLIT2, HSPA1A, FSHR, IL1R2 and CCND1.

Preferentially, said method assesses the eye irritation potential of a test compound, particularly when the bringing into contact of the test compound in step a) is carried out with the test compound in liquid form, wherein step b) comprises measuring the expression of the genes of the group consisting of: HSP90AA1, CASP1, DLK1, CLEC4D, IL24, SLIT2, HSPA1A, FSHR, IL1R2 and CCND1.

Preferentially, said method assesses the eye irritation potential of a test compound, particularly when the bringing into contact of the test compound in step a) is carried out with the test compound in solid form, wherein step b)

comprises measuring the expression of at least one gene selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least two genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least three genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least four genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least five genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least six genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least seven genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least eight genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least nine genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least ten genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least eleven genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of at least twelve genes selected from the group consisting of: IL-24, IL-23R, DDIT3, MMP8, DLK1, HAS1, CYR61, IL-1R2 CLEC4D, ICAM2, CASP1, MUC13 and MUC4.

Preferentially, said method assesses the eye irritation potential of a test compound, particularly when the bringing into contact of the test compound in step a) is carried out with the test compound in solid form, wherein step b) comprises measuring the expression of the genes of the group consisting of: IL-24, IL-23R, DDIT3, MMP8, DLK1, HAS1, CYR61, IL-1R2 CLEC4D, ICAM2, CASP1, MUC13 and MUC4.

In a particular embodiment of the method, in step a), the test compound brought into contact with the in vitro reconstructed corneal sample is in liquid or solid form. When the test compound is liquid, it may be used pure or diluted.

The compound may be diluted in a physiologically acceptable solvent such as phosphate-buffered saline (PBS), for example, and is therefore present at a mass concentration comprised between 0.1% and 100%. When the compound is diluted it is present at a mass concentration comprised between 10 and 60%, more particularly between 20 and 50%, more particularly between 25 and 40% and even more particularly 30%.

Step c) of the method comprises determining an eye irritation index of the compound.

More particularly, the determination of the eye irritation index of the compound comprises assigning an overexpression threshold value to each gene whose expression is measured.

The overexpression threshold value corresponds to a factor of increase in the expression of the gene when brought into contact with the test compound relative to the expression of said gene when brought into contact with a control.

Preferably, the method according to the present invention further comprises a step of comparing the expression level of said gene with a reference value. This reference value may be used as a positive and/or negative control.

A positive control, for example, may be performed by comparing the expression level of said at least one gene in the presence of the test compound with the expression level of said at least one gene in the presence of a compound known to be an eye irritant.

For example, if the expression level of said at least one gene in the presence of the test compound is greater than or equal to the expression level of said at least one gene in the presence of a compound whose irritant potential is known, it may be concluded that said compound has an irritant potential.

A negative control may be performed in the absence of the test compound or in the presence of a compound known to be non-irritating such as olive oil, 1,9-decadiene (CAS #1647-16-1), triclocarban (CAS #101-20-2) or the buffer in which the test product is dissolved or diluted when used in the method.

In the context of the present invention, it may be concluded that a test compound has eye irritant potential if overexpression of said gene is observed relative to its expression level in the absence of said test compound.

"Overexpression" means a significantly higher expression level of said gene relative to its normal expression level. Preferably, overexpression means an expression level in a biological sample that is at least 20% higher than the normal expression level of said gene (i.e., 1.2 times more), preferably at least 50% higher than the normal expression level of said gene (i.e., 1.5 times more), and particularly preferably at least 90% higher than the normal expression level of said gene (i.e., 1.9 times more).

The "expression level in the absence of said test compound" or "normal level" is the expression level of said gene in a control sample potentially corresponding to the biological sample of a tissue not exhibiting an irritation reaction or, preferably, to the average of the expression level of said gene in different control samples not exposed to the test compound.

Preferably, step b) is performed between 2 and 24 hours after step a), more preferably between 4 and 18 hours after step a), particularly preferably between 5 and 7 hours after step a) and even more preferably 6 hours after step a).

The control having a normal expression level consists in bringing into contact the in vitro reconstructed corneal sample with a non-irritating physiologically acceptable liquid, such as the liquid in which the test compound is dissolved or diluted, for example a buffer, more particularly PBS.

The threshold value indicating significant overexpression of the gene whose expression is measured may be comprised between 1.1 and 10, more particularly between 1.1 and 7, more particularly between 1.4 and 6, even more particularly between 2 and 5, still more particularly between 2 and 4.

As indicated above in one of the selected groups of genes, in the case of test compounds brought into contact in step a) in liquid form, the preferred genes are selected from the group comprising at least, or consisting of, HSP90AA1, CASP1, DLK1, CLEC4D, IL-24, SLIT2, HSPA1A, FSHR, IL-1R2 and CCND1.

For HSP90AA1, the overexpression threshold value is comprised between 1.1 and 2, more particularly 1.4.

For CASP1, the overexpression threshold value is comprised between 1.1 and 2, more particularly about 1.5.

For DLK1, the overexpression threshold value is comprised between 3 and 8, more particularly about 5, even more particularly 5.25.

For CLEC4D, the overexpression threshold value is comprised between 1.1 and 4, more particularly about 3.6.

For IL-24, the overexpression threshold value is comprised between 3 and 8, more particularly about 6.2.

For SLIT2, the overexpression threshold value is comprised between 1.1 and 2, more particularly about 1.3.

For HSPA1A, the overexpression threshold value is comprised between 1.1 and 5, more particularly about 3.

For FSHR, the overexpression threshold value is comprised between 1.1 and 4, more particularly about 2.6.

For IL-1R2, the overexpression threshold value is comprised between 1.1 and 2, more particularly about 1.3.

For CCND1, the overexpression threshold value is comprised between 1.1 and 2, more particularly about 1.5.

As indicated above for another group of possible genes, in the case of test compounds brought into contact in step a) in solid form, the preferred genes are selected from the group comprising at least, or consisting of, IL-24, IL-23R, DDIT3, MMP8, DLK1, HAS1, CYR61, IL-1R2 CLEC4D, ICAM2, CASP1, MUC13 and MUC4.

For IL-24, the overexpression threshold value is comprised between 1.5 and 15, more particularly between 2 and 10, more particularly 2.3.

For IL-24, the overexpression threshold value may also be comprised between 5 and 15, more particularly 10.

For IL-23R, the overexpression threshold value is comprised between 1.5 and 3, more particularly about 1.9.

For DDIT3, the overexpression threshold value is comprised between 1.5 and 3, more particularly about 5, even more particularly 2.

For MMP8, the overexpression threshold value is comprised between 1.1 and 2.5, more particularly about 1.4.

For DLK1, the overexpression threshold value is comprised between 2 and 8, more particularly about 4.

For HAS1, the overexpression threshold value is comprised between 1.5 and 5, more particularly about 3.

For CYR61, the overexpression threshold value is comprised between 1.1 and 2, more particularly about 1.3.

For IL-1R2, the overexpression threshold value is comprised between 1.4 and 3, more particularly about 2.

For CLEC4D, the overexpression threshold value is comprised between 1.5 and 3.5, more particularly about 2.8.

For ICAM2, the overexpression threshold value is comprised between 3 and 5, more particularly about 4.

For CASP1, the overexpression threshold value is comprised between 1.1 and 2, more particularly about 1.4.

For MUC13, the overexpression threshold value is comprised between 1.4 and 3, more particularly about 1.8.

For MUC4, the overexpression threshold value is comprised between 2 and 4, more particularly about 2.5.

The significant overexpression threshold value may, for each gene, be easily assessed and determined by a skilled person.

More specifically, the determination of the eye irritation index comprises assigning a weight value to each gene if the overexpression threshold value of said gene is reached following the expression measurement.

Thus, when the significant overexpression threshold of a given gene is reached, this gene is assigned a weight value that may be different or identical depending on the gene. This weight value may take discrete or continuous values, preferentially discrete values ranging from 1 to 10, namely selected from the group consisting of the values 1, 2, 3, 4, 5, 6, 7, 8, 9 and 10. More particularly, the discrete values may be selected from the group consisting of the values 1, 2, 3, 3, 4, 5. More particularly, said discrete values may be 1 or 2.

By way of illustration and without being in any way restrictive, the weight value may be limited to two values, or 2, which will be assigned to the gene when its significant overexpression threshold is reached or exceeded.

The choice to assign a higher or lower weight value depends on the nature of the gene in question and its involvement in the cellular stress response, in the metabolic pathway of interleukin, in the inflammatory process, in the regulation of cell growth, in wound healing, in cellular remodeling, for example, but also in the overexpression threshold value of the gene.

Also for illustrative purposes only and for the genes selected here chosen from the group comprising, or consisting of, HSP90AA1, CASP1, DLK1, CLEC4D, IL24, SLIT2, HSPA1A, FSHR, IL1R2 and CCND1; the weight value may take a value selected between 1 and 2.

For HSP90AA1, the weight value may be 2.
For CASP1, the weight value may be 2.
For DLK1, the weight value may be 2.
For CLEC4D, the weight value may be 2.
For IL24, the weight value may be 1.
For SLIT2, the weight value may be 1.
For HSPA1A, the weight value may be 2.
For FSHR, the weight value may be 2.
For IL-1R2, the weight value may be 1.
For CCND1, the weight value may be 2.

Similarly, and for the genes selected here chosen from the group comprising, or consisting of, IL-24, IL-23R, DDIT3, MMP8, DLK1, HAS1, CYR61, IL-1R2 CLEC4D, ICAM2, CASP1, MUC13 and MUC4; the weight value may take a value selected between 1 and 4.

For IL-24, with an overexpression threshold value of 2.3, the weight value may be 1.
For IL-24, with an overexpression threshold value of 10, the weight value may be 4.
For IL-23R, the weight value may be 4.
For DDIT3, the weight value may be 2.
For MMP8, the weight value may be 1.
For DLK1, the weight value may be 2.
For HAS1, the weight value may be 2.
For CYR61, the weight value may be 1.
For IL-1R2, the weight value may be 4.
For CLEC4D, the weight value may be 2.
For ICAM2, the weight value may be 4.
For CASP1 the weight value may be 2.
For MUC13, the weight value may be 3.
For MUC4, the weight value may be 4.

More particularly, the eye irritation index is determined by adding the weight values of genes whose expression exceeds the overexpression threshold value.

The method according to the invention may also comprise a step of categorizing the test compound comprising assigning an irritation category to the test compound based on the value of the eye irritation index obtained.

The method according to the invention thus provides the skilled person with a predictive method for classifying a compound according to its eye irritation potential by following the European classification, namely not irritant, reversible irritant or irreversible irritant.

The results presented in the experimental section of the present application demonstrate this advantage of the invention, and the superiority of this method over existing ones is evident from these results.

EXAMPLES

Materials and Methods

Reconstructed Human Corneal Epithelium Model (SkinEthic™ HCE)

The reconstructed human corneal epithelium model, (SkinEthic™ HCE) was purchased from Episkin in Lyon. The model consists of immortalized human corneal epithelial cells grown in a defined medium at the air-liquid interface. The tissue structure obtained is a multi-layer epithelium similar to the natural tissue structure of the human cornea, comprising 5-7 layers with a surface area of 0.5 $cm^2$.

Polyhedral cells and wing cells are also present. The tissue also comprises specific ultrastructures such as intermediate filaments, mature hemidesmosomes and desmosomes. The 65-kD cytokeratin (K3) was also detected (Nguyen et al., 2003). The tissues are shipped on a semisolid layer of agarose culture medium. Upon receipt, the tissues are transferred to maintenance medium (1 ml/well) in 6-well plates and incubated in a climatic chamber at 37° C., 5% $CO_2$. The tissues are used 24 hours later.

Chemicals

All the chemicals tested were purchased from Sigma, France. The purity was higher than 87% for all the chemicals tested, which covered a wide range of potential eye irritants.

Preparation of Liquid Chemicals

Liquid products are tested for solubility in phosphate-buffered saline (PBS) or olive oil. In summary, 100 µl of the test product is mixed with 200 µl of PBS or olive oil.

The sample is mixed on a vortex mixer. Turbidity and possible phase separation are assessed by eye. The products are tested pure or diluted to 30%. Products that are not soluble in PBS or olive oil cannot be tested at 30%.

Treatment Protocol for Liquid Products

The procedure for applying liquid products to the tissues was optimized as follows: the chemicals are tested at two concentrations, 100% and 30%. In summary, the tissue surface is moistened by adding 20 µl of PBS at 37° C. and incubation for 10 min at 37° C./5% $CO_2$. The corneal epithelia are then treated topically with 50±2 µL of the test product (corresponding to 100 µL/cm2) and incubated for 10 min at room temperature. The tissues are then washed with sterile PBS (2×25 ml) at 37° C. PBS is applied to the edge of the insert (not directly on the tissue) to create a gentle vortex that removes the chemical. The tissues on their inserts are then "embedded" in 5 ml of maintenance medium at room temperature for 30 min in order to remove as much as possible of the product remaining on the tissue surface. The medium is then removed by gently tapping the insert on absorbent paper, and 50 µl of maintenance medium at 37° C. is added. The inserts are then incubated for 6 h at 37° C./5% $CO_2$.

Treatment Protocol for Solid Products

The procedure for applying solid (powdered) products to the tissues was optimized as follows. First, the products are reduced to the finest possible powder with a mortar. The chemicals are tested at a single dose. In summary, the tissue surface is moistened by adding 20 µl of PBS at 37° C. and incubation for 10 min at 37° C./5% $CO_2$. The corneal epithelia are then treated topically with 30±2 mg (representing 60 mg/cm2) and incubated for 30 min at room temperature. The tissues are then washed with sterile PBS (2×25 ml) at 37° C. PBS is applied to the edge of the insert (not directly on the tissue) to create a gentle vortex that removes the chemical. The tissues on their inserts are then "embedded" in 5 ml of maintenance medium at room temperature for 30 minutes in order to remove as much as possible of the product remaining on the tissue surface. The medium is then removed by gently tapping the insert on absorbent paper, and 50 µl of maintenance medium at 37° C. is added. The inserts are then incubated for 6 h at 37° C./5% $CO_2$.

Purification of Total RNA

The total RNA purification process was described by Cottrez et al., 2015. In summary, corneal tissues are recovered with forceps and placed in tubes for rapid freezing in liquid nitrogen. The RNA is then extracted by the QIAzol technique (Qiagen, Courtaboeuf, France) with an "RNeasy Mini Kit" according to the manufacturer's instructions. In summary, the tissues are placed in 1 ml of QIAzol and homogenized using the TissueLyser II (Qiagen, Courtaboeuf, France) with 2 steel beads. After centrifugation, the supernatant is collected and 0.2 ml of bromochloro propane (Sigma, France) is added, then the whole is vigorously mixed. The homogenate is centrifuged at 12,000 g for 15 min at 4° C. The upper phase (aqueous phase) is added to 600 µl of 70% ethanol and immediately mixed by pipetting. The mixture is transferred to an RNeasy spin column placed on a 2 ml collection tube and the RNA is collected according to the manufacturer's instructions (Qiagen, Courtaboeuf, France).

Quantitative RT-PCR Analysis

The quantitative RT-PCR procedure was described by Cottrez et al., 2015. In summary, the transcription of total RNA is performed with 1 µg of total RNA in a final volume of 20 µl using "Random Primers" (Invitrogen, France) and "SuperScript III Reverse Transcriptase" (Invitrogen, France) according to the manufacturer's instructions. Quantitative RT-PCR uses a PCR reagent mix: SYBR Green Real-Time PCR Master Mix (ROCHE, France) with 0.4 µM of each nucleotide primer in a final volume of 25 µl. The reaction is performed in an LC480 System (ROCHE, France). The amplification program comprises a cycle at 95° C. for 1 min, followed by 40 cycles with denaturation at 95° C. for 15 s, a hybridization and amplification phase at 60° C. for 15 s, followed by a final elongation phase at 72° C. for 40 s.

The relative amount of each transcript is normalized to the average amount of expression of 5 so-called housekeeping genes (Glucuronidase β-GUSB, vacuolar ATPase-ATP6V0E1, H2A Histone Family, Member Y-H2AFY, Glucose-6-Phosphate Dehydrogenase-G6PD and "non-POU domain-containing, octamer-binding"-NONO).

Data Analysis
Measurement of Gene Expression

The gene expression rate is measured by an absolute quantification analysis method using an algorithm based on the maximum of the second derivative developed by Roche. The relative overexpression rate (fold increase) is then calculated in relation to tissues treated with PBS alone.

Definition of the Prediction Model for the Eye Irritation Test for Liquids

The expression of 10 genes (i.e., HSP90AA1, CASP1, DLK1, DLK1, CLEC4D, IL-24, SLIT2, HSPA1A, FSHR, IL-1R2, CCND1 (marked with stars in FIG. 1) is measured in corneal epithelium models after application of either a 100% or a 30% dose of the test product as indicated above. The significant overexpression values were set for each of the genes at 1.4, 1.5, 5.25, 3.6, 6.2, 1.3, 3, 2.6, 1.3 and 1.5, respectively. Each overexpressed gene then receives a set value of 2, 2, 2, 2, 1, 1, 2, 2, 1 or 2, respectively. An eye irritation index for liquid substances (LII: Liquid Irritation Index) is then calculated by adding the values assigned to each overexpressed gene for a maximum value of 17. When, after the tissues are treated with the tested product, tissue destruction is considered too high (the total RNA collected represents less than 10% of the amount of RNA collected in the PBS-treated tissues) an LII value of 20 is assigned.

The prediction and classification model works as follows. Each product is tested at 100% and 30% (see above). If LII≥10 at 100% and 30%, the tested product is classified as "Cat I". If LII 10 at 100% and <10 at 30%, the tested product is classified as "Cat 2". If LII<10 at 100% and 30%, the tested product is classified as "No-Cat".

Definition of the Prediction Model for the Eye Irritation Test for Solids

The expression of 13 genes (i.e., IL-24, IL-23R, DDIT3, MMP8, DLK1, HAS1, CYR61, IL-1R2 CLEC4D, ICAM2, CASP1, MUC13, MUC4 (marked with stars in FIG. 2)) is measured in corneal epithelium models after applying a dose of 60 mg/cm$^2$ of the test product as indicated above. The significant overexpression values were set for each of the genes at respectively 2.3 and 10 for IL-24, then for each of the other genes in order 1.9, 2, 1.4, 4, 3, 1.3, 2, 2.8, 4, 1.4, 1.8 and 2.5. Each overexpressed gene (or each threshold exceeded for IL-24) is then given a set value of 1, 4, 4, 2, 1, 2, 2, 1, 4, 2, 4, 2, 3 and 4, respectively. An eye irritation index for solid substances (SII: Solid Irritation Index) is then calculated by adding the values assigned to each overexpressed gene for a maximum value of 36. When, after the tissues are treated with the tested product, tissue destruction is considered too high (the total RNA collected represents less than 10% of the amount of RNA collected in the PBS-treated tissues) an SII value of 40 is assigned.

The prediction and classification model works as follows. Each product is tested at 60 mg/cm$^2$ (see above). If SII 20 the tested product is classified as "Cat I". If 10≤SII<20 the tested product is classified as "Cat 2". If SII<10 the tested product is classified "No-Cat".

Acceptability Criteria for Liquids

Two "control" chemicals are tested in parallel with the tested products. A non-irritant: 1,9-decadiene (CAS #1647-16-1) tested at 100%, and a Category 2 product: 2-methyl-1-pentanol (CAS #105-30-6) tested at 100% and 30%. The test is considered valid if the LII values obtained for 1,9-decadiene tested at 100% and 2-methyl-1-pentanol tested at 30% are less than 10 and if the LII for 2-methyl-1-pentanol tested at 100% is >10.

Each chemical is tested twice on two different batches of corneal epithelial tissue. If these two analyses have given the same classification, the test is considered valid, otherwise a third or fourth analysis is performed.

Acceptability Criteria for Solids

Two "control" chemicals are tested in parallel with the products tested. A non-irritant: triclocarban (CAS #101-20-2) and a Category 2 product: naphthalene dione (CAS #83-56-7). The test is considered valid if the SII value obtained for triclocarban is <10 and the value obtained for naphthalene dione is comprised between 10 and 20.

Each chemical is tested twice on two different batches of corneal epithelial tissue. If these two analyses have given the same classification, the test is considered valid, otherwise a third or fourth analysis is performed.

Statistical Analysis
Cooper Statistics

The values of the statistical analysis according to Cooper (Sensitivity, Specificity and Accuracy) (Cooper et al., 1979) are calculated for the eye irritation test using as a reference the literature data for the Draize test (Barroso et al., 2016). A 2×2 contingency table with irritants and non-irritants as parameter is constructed using the results obtained with the eye irritation test. Sensitivity, Specificity and Accuracy are then calculated using the recommendations of Cooper (Cooper et al., 1979).

Confusion Matrix Analysis

For statistics using confusion matrices and Kappa calculation we used the recommendations of Landis and Koch (Landis and Koch, 1977).

Results
Selection of Biomarker Genes for Mechanisms of Eye Irritation

To identify the genes involved in the mechanisms of eye irritation, we used a data analysis tool developed in collaboration with Dieng-Kuntz et al. (Dieng-Kuntz et al., 2006). A first group of 900 genes was selected. From this large group of candidate genes, we have selected genes whose expression is modulated in samples taken from the surface of the human eye by a conjunctival impression device (Roy et al., 2013). Then we used an analysis of the gene expression obtained after using a group of 10 chemicals (Table 1 #1-10) applied to the Skinethic HCE tissue model, combined with a data mining search of the existing literature. This analysis allowed us to define a group of 92 genes involved in the mechanisms that lead to eye irritation (Table 2).

Development of the Prediction Model for the Eye Irritation Test for Liquids

Changes in the expression of the 92 genes that we selected as representatives of potential candidate biomarkers (Table 2) were analyzed after treatment with 39 chemicals (Table 1). Using a subgroup of 29 genes: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61 (FIG. 1) it was possible to classify the 39 chemicals into one of the 3 categories of eye irritation implemented by the UN-GHS standard. However, since some of the genes had a redundant role and could substitute for each other, we were able to select a subgroup of 10 genes to develop a liquid irritation index (LII) capable of discriminating between the 3 categories of irritants. The list of genes selected for the liquids included: HSP90AA1, CASP1, DLK1, CLEC4D, IL-24, SLIT2, HSPA1A, FSHR, IL-1R2 and CCND1 (shown in FIG. 1). The LII was developed in two stages. First, we selected a threshold value for each gene to demonstrate significant overexpression. Different threshold values were tested, and the optimal values retained for these 10 genes were respectively 1.4, 1.5, 5.25, 3.6, 6.2, 1.3, 3, 2.6, 1.3 and 1.5. We then assigned a weight to these values based on the importance of the overexpression of the gene in question in the mechanisms of eye irritation. Each gene overexpressed above the threshold value then received a weighted value of 2, 2, 2, 2, 1, 1, 2, 2, 1 and 2, respectively. The LII is then calculated by adding the weight values for each of the overexpressed genes with a maximum of 17. When the level of tissue destruction is considered too high (see Materials and Methods) a value of 20 is applied.

Analysis of the Results Obtained by the Eye Irritation Test with the 39 Liquid Products Tested.

The classification predictions obtained with the eye irritation tests on the 39 chemicals (Table 3) were compared to those obtained with the Draize test in a 2×2 contingency table to assess the predictive ability of the test to first distinguish irritant products (Cat 1 and Cat 2) from non-irritant products (No-Cat) (Table 4). Specificity, sensitivity and accuracy of 100% were obtained on this group of 39 chemicals.

We then analyzed a confusion matrix containing 3 classes (Cat 1, Cat 2 and No-Cat, see Table 5) to calculate the performance of the test to classify the products according to UN-GHS standards. A user accuracy of 91.66%, 93.33% and 100% was obtained for Cat 1, Cat 2 and No-Cat products, respectively. With an overall accuracy of 95% and a highly significant kappa of 0.923.

These results show that the eye irritation test is very effective in classifying the eye irritation potential of liquid chemicals into the 3 classes defined by the UN-GHS standard.

Development of the Prediction Model for the Eye Irritation Test for Solids

Figure 2:
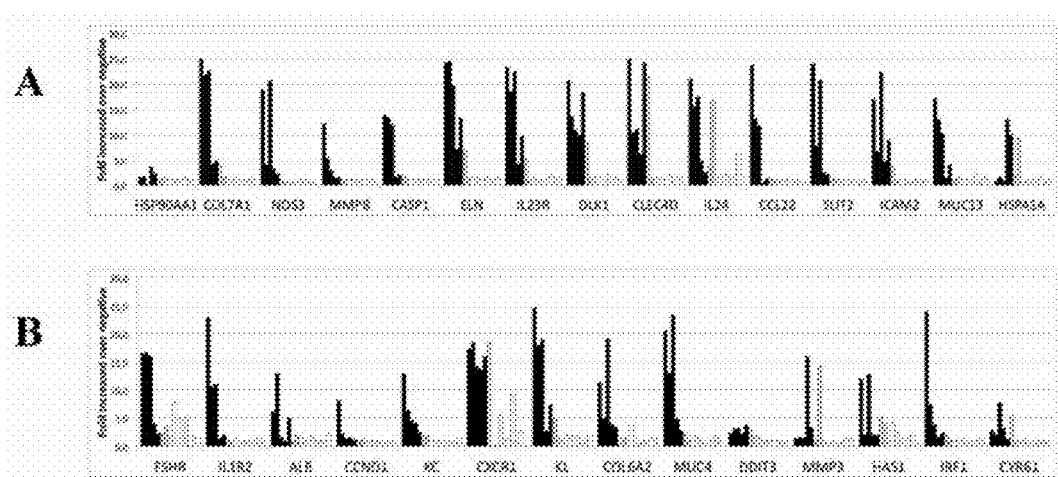

For solids we tested 15 chemicals (Table 6). Using the same group of 29 genes: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1, CYR61 (FIG. 2) it was possible to classify the 15 chemicals into one of the 3 categories of eye irritation implemented by the UN-GHS standard. However, since some of the genes had a redundant role and could substitute for each other, we were able to select a subgroup of 13 genes to develop a solid irritation index (SII) capable of discriminating between the 3 categories of irritants. The list of genes selected for solids includes: (IL-24, IL-23R, DDIT3, MMP8, DLK1, HAS1, CYR61, IL-1R2, CLEC4D, ICAM2, CASP1, MUC13, MUC4. FIG. 2). The SII was developed in two stages. First, we selected a threshold value for each gene to demonstrate significant overexpression. Different threshold values were tested, and the optimal values retained for these 13 genes were respectively 2.3 and 10 for IL-24, then for each of the other genes in order 1.9, 2, 1.4, 4, 3, 1.3, 2, 2.8, 4, 1.4, 1.8 and 2.5. We then assigned a weight to these values based on the importance of the overexpression of the gene in question in mechanisms of eye irritation. Each gene overexpressed above the threshold value then received a weighted value of respectively 1, 4, 4, 2, 1, 2, 2, 1, 4, 2, 4, 2, 3 and 4. The SII is then calculated by adding the weight values for each of the overexpressed genes with a maximum of 36. When the level of tissue destruction is considered too high (see Materials and Methods) a value of 40 is applied.

Analysis of the Results Obtained by the Eye Irritation Test with the 15 Solid Products Tested.

The classification predictions obtained with the eye irritation tests on the 15 solid chemicals (Table 7) were compared to those obtained with the Draize test in a 2×2 contingency table to assess the predictive ability of the test to first distinguish irritant products (Cat 1 and Cat 2) from non-irritant products (No-Cat) (Table 8). Specificity, sensitivity and accuracy of 100% were obtained on this group of 15 chemicals.

We then analyzed a confusion matrix containing 3 classes (Cat 1, Cat 2 and No-Cat, see Table 9) to calculate the performance of the test to classify the products according to UN-GHS standards. 100% user accuracy was obtained for products classified as Cat 1, Cat 2 and No-Cat. With a general accuracy of 100% and a perfectly significant kappa of 1.

These results show that the eye irritation test is very effective in classifying the eye irritation potential of chemicals in the 3 classes defined by the UN-GHS standard.

FIGURE LEGENDS

FIG. 1 A, B, C, D: Analysis of gene expression in 3D reconstructed human corneal tissue treated with various irritant and non-irritant liquid chemicals.

The value of the overexpression rate (fold increase) for the 29 genes indicated was represented for 4 category 1 chemicals (black bars, in order from left to right: lactic acid, methyl thioglycolate, sodium lauryl sulfate (15%), benzalkonium chloride (10%)), 4 category 2 chemicals (grey bars, in order from left to right: alpha hexyl cinnamaldehyde, acetone, methyl ethyl ketone, 3-chloro propane nitrile) and 4 unclassified products (No category, white bars in order from left to right: 1,9-decadiene, glycerol, Tween 20, 2,4-pentanediol). Each chemical was applied at 100% (A and B) or diluted to 30% (C and D). The genes used for the example are HSP90AA1, CASP1, DLK1, CLEC4D, IL-24, SLIT2, HSPA1A, FSHR, IL-1R2 and CCND1.

FIG. 2 A and B: Analysis of gene expression in 3D reconstructed human corneal tissue treated with different irritant and non-irritant solid chemicals.

The value of the overexpression rate (fold increase) for the 29 genes indicated was represented for 5 category 1 chemicals (black bars, in order from left to right: 2-hydroxy-isobutyric acid, promethazine hydrochloride, sodium oxalate, 2,5-dimethyl hexanediol, 1-naphthalene acetic acid), 2 category chemicals (grey bars, in order from left to right: naphthalene diol, camphene) and 8 unclassified products (No category, white bars in order from left to right: triclocarban, methylene-bis benzotriazol tetramethylbutyl phenol, pyrimethanil, myristyl myristate, 4,4'-methylene bis-(2,6-di-tert-butylphenol), 4-bromophenetol, potassium tetrafluoroborate). Each chemical was applied pure in powder form (30±2 mg (representing 60 mg/cm$^2$)). The genes selected for the example are IL-24, IL-23R, DDIT3, MMP8, DLK1, HAS1, CYR61, IL-1R2 CLEC4D, ICAM2, CASP1, MUC13, MUC4.

TABLE 1

List of liquid products studied

| No | Chemical | CAS RN | UN GHS |
|----|----------|--------|--------|
| 1 | Triton X100 10% | 9002-93-1 | Cat 1 |
| 2 | Triton X100 5% | 9002-93-1 | Cat 2A |
| 3 | Triton X100 1% | 9002-93-1 | No Cat |
| 4 | Sodium lauryl sulfate 3% | 151-21-3 | No Cat |
| 5 | Methyl ethyl ketone | 78-93-3 | Cat 2A |
| 6 | Acetone 100% | 67-64-1 | Cat 2A |
| 7 | Lactic acid | 50-21-5 | Cat 1 |
| 8 | Chlorhexidine 50% | 55-56-1 | Cat 1 |
| 9 | Benzalkonium chloride 5% | 8001-54-5 | Cat 1 |
| 10 | Hexadecyltrimethylammonium bromide 10% | 57-09-0 | Cat 1 |
| 11 | Triton X-100 10% | 9002-93-1 | Cat 1 |
| 12 | Benzethonium chloride 10% | 121-54-0 | Cat 1 |
| 13 | Methyl thioglycolate | 2365-48-2 | Cat 1 |
| 14 | Diethylaminopropionitrile | 5351-04-2 | Cat 1 |
| 15 | Tetraethylene glycol diacrylate | 17831-71-9 | Cat 1 |
| 16 | 1-Chloroctan-8-ol | 23144-52-7 | Cat 1 |
| 17 | [3-(2-Aminoethylamino)propyl]trimethoxysilane | 1760-24-3 | Cat 1 |
| 18 | Sodium hydroxide 0.3% | 1310-73-2 | Cat 2A |
| 19 | 2,6-Dichlorobenzoyl chloride | 4659-45-4 | Cat 2A |
| 20 | Gamma-butyrolactone | 96-48-0 | Cat 2A |
| 21 | Allyl alcohol | 107-18-6 | Cat 2A |
| 22 | Chlorhexidine gluconate (20%) | 18472-51-0 | Cat 2A |
| 23 | Propasol Solvent P | 1569-01-3 | Cat 2A |
| 24 | 2-Methyl-1-pentanol | 105-30-6 | Cat 2B |
| 25 | iso-Butanal | 78-84-2 | Cat 2B |
| 26 | 3-Chloropropionitrile | 542-76-7 | Cat 2B |
| 27 | Ethyl-2-methylacetoacetate | 609-14-3 | Cat 2B |
| 28 | Glycolic acid (10%) | 79-14-1 | Cat 2B |
| 29 | Diethyl toluamide | 134-62-3 | Cat 2B |
| 30 | Glycerol | 56-81-5 | No Cat |
| 31 | Tween 20 | 9005-64-5 | No Cat |
| 32 | Octyltrimethoxysilane (SILAN 108) | 3069-40-7 | No Cat |
| 33 | 1,9-Decadiene | 1647-16-1 | No Cat |
| 34 | 2,4-Pentanediol | 625-69-4 | No Cat |
| 35 | 2-Ethoxyethyl methacrylate | 2370-63-0 | No Cat |
| 36 | Dipropyl disulfide | 629-19-6 | No Cat |
| 37 | n-Hexyl bromide | 111-25-1 | No Cat |
| 38 | Polyoxyethylene hydrogenated castor oil (Kolliphor) | 61788-85-0 | No Cat |
| 39 | 1-Ethyl-3-methylimidazolium ethylsulfate | 342573-75-5 | No Cat |

TABLE 2

List of genes analyzed by RT-PCR

| SYMBOL | DESCRIPTION | Function | REFSEQ |
|--------|-------------|----------|--------|
| ALB | Albumin | Major corneal protein | NM_000477 |
| ATP6V0E1 | ATPase, H+ transporting, lysosomal 9 kDa, V0 subunit e1 | Involved in oxidative phosphorylation and phagosome | NM_003945.3 |

TABLE 2-continued

List of genes analyzed by RT-PCR

| SYMBOL | DESCRIPTION | Function | REFSEQ |
|---|---|---|---|
| B4GALT6 | UDP-Gal:betaGlcNAc beta 1,4-galactosyltransferase, polypeptide 6 | Required for glycophospholipid biosynthesis. Expressed more in the cornea than other family members. | NM_004775 |
| CASP1 | caspase 1, apoptosis-related cysteine peptidase (interleukin 1, beta, convertase) | IL-1 activation. | NM_033292 |
| CCL22 | chemokine (C-C motif) ligand 22 | CCR4 ligand; involved in the transit of T cells. | NM_002990.3 |
| CCND1 | cyclin D1 | Positive cell cycle regulator | NM_053056 |
| CCNF | cyclin F | Cell cycle regulator | NM_001761.2 |
| CCS | copper chaperone for superoxide dismutase | Deliver copper to copper-dependent zinc superoxide dismutase (SOD1) | NM_005125125 |
| CLEC4D | C-type lectin domain family 4, member D | Endocytic receptor. Involved in the handling of antigens. | NM_080387.4 |
| COL17A1 | collagen, type XVII, alpha 1 | Plays a role in the attachment of basal keratinocytes to the basal membrane. | NM_000494 |
| COL6A2 | collagen type VI alpha 2 | Acts as a cell binding protein | NM_001849.3 |
| COL7A1 | collagen, type VII, alpha 1 | Stratified squamous epithelial membrane protein. | NM_00000094 |
| COL8A2 | collagen, type VIII, alpha 2 | Major component of the Descemet membrane of corneal endothelial cells. Markers of human corneal endothelial cells. | NM_005202.2 |
| CRYAB | crystalline, alpha B | May contribute to the transparency and refractive index of the lens | NM_001885 |
| CSF2 | colony stimulating factor 2 (granulocyte-macrophage) | Hematopoietic cell growth factor | NM_000758.2 |
| CTGF | connective tissue growth factor | Major micro attractive connective tissue secreted by vascular endothelial cells. | NM_001901.2 |
| CTSZ | cathepsin Z | Proteinase cysteine involved in lysosomal and extracellular protein degradation | NM_001336.2 |
| CXCL1 | chemokine (C—X—C motif) ligand 1 (melanoma growth stimulating activity, alpha) | Has chemotactic activity for neutrophils. | NM_001511.1 |

TABLE 2-continued

List of genes analyzed by RT-PCR

| SYMBOL | DESCRIPTION | Function | REFSEQ |
| --- | --- | --- | --- |
| CXCL9 | chemokine (C—X—C motif) ligand 9 | Has chemotactic activity for T cells. Binds to CXCR3 | NM_002416.1 |
| CXCR1 | chemokine (C—X—C motif) receptor 1 | Interleukin-8 receptor, a chemotactic factor of neutrophils. | NM_000634.2 |
| CYR61 | cysteine-rich, angiogenic inducer, 61 | Involved in corneal neovascularization | NM_001554.4 |
| CYYR1 | cysteine/tyrosine-rich 1 | Specific marker for human corneal endothelial cells. | NM_052954.2 |
| DDIT3 | DNA-damage-inducible transcript 3 | Apoptosis marker | NM_004083.4 |
| DEFB1 | defensin, beta 1 | Involved in mucosal defense against aggression | NM_005218 |
| DLK1 | delta-like 1 homolog (*Drosophila*) | Non-canonical ligand involved in tissue development | NM_003836 |
| DUOX2 | Dual oxidase 2 | Member of the NADPH oxidase family | NM_014080 |
| DUSP6 | dual specificity phosphatase 6 | Targets the ERK family and plays a role in corneal cell proliferation. | NM_001946.21 |
| ELN | elastin | Major protein of tissue structure. | NM_000501.2 |
| ESR1 | estrogen receptor 1 | Hormonal nuclear receptor. Affects cell proliferation and target tissue differentiation. | NM_000125 |
| FBN1 | fibrillin 1 | Fibrillins are structural components sometimes associated with elastin. | NM_000138 |
| FBN2 | fibrillin 2 | Fibrillins are structural components sometimes associated with elastin | NM_001999 |
| FDXR | ferredoxin reductase | mitochondrial flavoprotein that initiates electron transport for cytochromes P450 receiving electrons from NADPH | NM_004110.3 |
| FGF2 | fibroblast growth factor 2 (basic) | Growth factor and angiogenic agent. | NM_002006 |
| FGFR1 | fibroblast growth factor receptor 1 | Fibroblast growth factor (FGF1 and FGF2) receptor | NM_015850 |
| FOS | FBJ murine osteosarcoma viral oncogene homolog | Nuclear phosphoprotein forming a strong but non-covalent complex with the transcription factor JUN/AP-1. | NM_005252 |
| FOXO1 | forkhead box 01 | Transcription factor involved in insulin metabolic pathways | NM_002015 |

TABLE 2-continued

List of genes analyzed by RT-PCR

| SYMBOL | DESCRIPTION | Function | REFSEQ |
|---|---|---|---|
| FSHR | follicle stimulating hormone receptor | Follicle-stimulating hormone (FSH) receptor. | NM_000145 |
| FST | follistatin | FSH inhibitor | NM_013409.2 |
| G6PD | Glucose-6-phosphate dehydrogenase | Produces pentoses for nucleic acid synthesis and main producer of NADPH reducing power | NM_000402 |
| GAA | Glucosidase, alpha; acid | Essential for the degradation of glycogen to glucose in lysosomes. | NM_000152.3 |
| GSTT1 | Glutathione S-transferase theta 1 | Conjugation of reduced glutathione with many exogenous and endogenous electrophilic compounds. | NM_000853.2 |
| GUSB | glucuronidase, beta | Important role in the degradation of dermatan sulfates and keratan sulfates. | NM_000181 |
| H2AFY | H2A histone family, member Y | A variant of the histone H2A replacing conventional H2A in a subgroup of nucleosomes where it suppresses transcription. | NM_138610.2 |
| HAS1 | hyaluronan synthase 1 | Plays a role in the synthesis of hyaluronan and hyaluronic acid. | NM_001523 |
| HSP90AA1 | heat shock protein 90 kDa alpha (cytosolic), class A member 1 | Molecular chaperone that promotes the maturation, maintenance, structure and regulation of specific target proteins involved in cell cycle control and signal transduction | NM_005348 |
| HSPA1A | heat shock 70 kDa protein 1A | Hsp70s stabilizes proteins against aggregation and helps to fold new peptides translated in the cytosol and organelles. | NM_005345 |
| ICAM2 | intercellular adhesion molecule 2 | ICAMs are the ligands for the adhesion of LFA-1 proteins to leukocytes. | NM_001099789.1 |
| IER3 | immediate early response 3 | May play a role in the ERK signal by inhibiting the dephosphorylation of ERK by phosphatase PP2A-PPP2R5C holoenzyme | NM_003897.3 |
| IGFBP2 | insulin-like growth factor binding protein 2, 36 kDa | Inhibits IGF-mediated development and growth. | NM_000597.2 |

TABLE 2-continued

List of genes analyzed by RT-PCR

| SYMBOL | DESCRIPTION | Function | REFSEQ |
| --- | --- | --- | --- |
| IL-17C | interleukin 17C | Stimulates the release of tumor necrosis factor alpha and IL-1beta from the monocytic cell line THO-1. | NM_013278 |
| IL-1 R2 | interleukin 1 receptor, type II | Receptor of interleukin-1 alpha (IL-1A), beta (IL-1B) and the interleukin-a receptor antagonist protein (IL-1ra). | NM_173343.1 |
| IL-23R | interleukin 23 receptor | Combines with IL12RB1 to form the interleukin-23 receptor. | NM_144701.2 |
| IL-24 | interleukin 24 | Role in wound healing | NM_181339.1 |
| IRF1 | interferon regulatory factor 1 | Specifically binds to the upstream regulatory region of type I IFN and MHC IFN genes and activates these genes. | NM_002198 |
| ITGA6 | integrin, alpha 6 | Integrin alpha-6/beta-4 is a laminin receptor in epithelial cells and plays a critical structural role in the hemidesmosome. | NM_000210.2 |
| ITGA7 | integrin, alpha 7 | Integrin alpha-7/beta-1 is the primary laminin receptor in skeletal myoblasts and adult myofibers. | NM_002206 |
| JUN | jun protooncogene- | Transcription factor that recognizes and binds to the heptamer motif 5'-TGA[CG]TCA-3'. | NM_002228 |
| KL | klotho | Involved in the aging process | NM_004795 |
| KRT1 | keratin 1 | member of the keratin family | NM_006121.3 |
| KRT14 | keratin 14 | member of the keratin family | NM_000526.4 |
| KRT15 | keratin 15 | member of the keratin family | NM_002275.3 |
| KRT17 | keratin 17 | member of the keratin family | NM_000422.2 |
| KRT19 | keratin 19 | member of the keratin family | NM_002276.4 |
| KRT3 | keratin 3 | member of the keratin family | NM_057088.2 |
| KRT5 | keratin 5 | member of the keratin family | NM_000424 |
| KRT9 | keratin 9 | member of the keratin family | NM_000226.2 |
| MMP10 | matrix metallopeptidase 10 (stromelysin 2) | May degrade fibronectin, gelatins type I, III, IV and V. | NM_002425.1 |
| MMP13 | matrix metallopeptidase 13 (collagenase) | Degrades type I collagen. No action on gelatin or casein. | NM_002127.2 |

TABLE 2-continued

List of genes analyzed by RT-PCR

| SYMBOL | DESCRIPTION | Function | REFSEQ |
|---|---|---|---|
| MMP3 | matrix metallopeptidase 3 (stromelysin 1, progelatinase) | Degrades fibronectin, laminin, gelatins type I, III, IV, IV, and V; collagens III, IV, X, and IX, and proteoglycans of cartilage. | NM_002422.3 |
| MMP8 | matrix metallopeptidase 8 (neutrophil collagenase) | Degrades fibrillar collagen types I, II and III. | NM_00242424.2 |
| MSN | moesin | Involved in the connections of major cytoskeletal structures of the plasma membrane. | NM_002444.2 |
| MSRA | Methionine sulfoxide reductase A | Functions as a repair enzyme for proteins inactivated by oxidation. | NM_012331 |
| MUC1 | mucin 1, cell surface associated | Expressed by apical cells and plays a role in tear film | NM_001204285.1 |
| MUC13 | mucin 13, cell surface associated | Expressed by apical cells and plays a role in tear film | NM_033049 |
| MUC16 | mucin 16, cell surface associated | Expressed by apical cells and plays a role in tear film | NM_024690 |
| MUC4 | mucin 4, cell surface associated | Expressed by apical cells and plays a role in tear film | NM_018406 |
| MYD88 | myeloid differentiation primary response gene (88) | Protein involved in the signaling pathways of the Toll-like and IL-1 receptor | NM_001172569.1| |
| NONO | non-POU domain containing, octamer-binding | DNA and RNA binding proteins; involved in many nuclear processes. | NM_007363 |
| NOS3 | nitric oxide synthase 3 (endothelial cell) | Product of NO involved in vascular relaxation of smooth muscle. | NM_000603 |
| OCLN | occludin | Role in the formation and regulation of tight junctions, paracellular barrier of permeability. | NM_002538.3 |
| PER1 | period homolog 1 (*Drosophila*) | Component of the circadian mechanism essential for the generation of circadian rhythms. | NM_002616 |
| RAD23A | RAD23 homolog A (*S. cerevisiae*) | Multiubiquitin receptor involved in the modulation of proteasome degradation | NM_00505353 |
| S100A4 | S100 calcium binding protein A4 | — | NM_002961.2 |

TABLE 2-continued

List of genes analyzed by RT-PCR

| SYMBOL | DESCRIPTION | Function | REFSEQ |
|---|---|---|---|
| SIRT6 | sirtuin 6 | NAD-dependent deacetylase. Modulates the acetylation of H3 histones at the telomeric chromatin during the S phase of the cell cycle. | NM_016539 |
| SIRT7 | sirtuin 7 | NAD-dependent deacetylase. Required to restore the transcription of rRNA at the end of mitosis. | NM_016538 |
| SLC4A11 | solute carrier family 4, sodium borate transporter, member 11 | Transporter playing an important role in the transport of sodium mediated fluid in different organs. Prevents severe morphological changes caused by increased NaCl concentrations in the stroma. | NM_001174090.1 |
| SLIT2 | slit homolog 2 (*Drosophila*) | Acts as a molecular guide in cell migration and appears to be modulated by interaction with homologous receptors. | NM_004787 |
| SNN | stannin | Plays a role in the toxic effects of organotins. | NM_003498 |
| STK25 | serine/threonine kinase 25 | Stress activated oxidative serine/threonine kinase that may play a role in the response to environmental stress. | NM_006374.3 |
| THBS1 | thrombospondin 1 | Adhesive glycoprotein mediating cell-cell and cell-matrix interactions. Binds to heparin. | NM_003246 |
| TNFAIP3 | tumor necrosis factor, alpha-induced protein 3 | Ubiquitin-dependent editing enzyme containing ubiquitin-ligase and deubiquitinase activities. | NM_006290.2 |
| TPSAB1 | tryptase alpha/beta 1 | Tryptase is a major protease present in mast cells and secreted during the response by degranulation/activation of this type of cell. | NM_003294.3 |

TABLE 3

Results of the analysis of the 39 liquid products tested by the eye irritation test (EIT) and comparison with the results obtained by the Draize test

| No | Chemical | CAS RN | Irritation INDEX | 100% 30% | EIT prediction | UN-GHS |
|---|---|---|---|---|---|---|
| 1 | Triton X100 10% | 9002-93-1 | 13<br>12 | 15<br>13 | —<br>— | Cat 1 | Cat 1 |
| 2 | Triton X100 5% | 9002-93-1 | 12<br>6 | 13<br>8 | —<br>— | Cat 2 | Cat 2A |
| 3 | Triton X100 1% | 9002-93-1 | 8<br>5 | 7<br>4 | —<br>— | No Cat | No Cat |
| 4 | Sodium lauryl sulfate 3% | 151-21-3 | 9<br>9 | 7<br>7 | —<br>— | No Cat | No Cat |
| 5 | Methyl ethyl ketone | 78-93-3 | 12<br>8 | 11<br>7 | —<br>— | Cat 2 | Cat 2A |
| 6 | Acetone 100% | 67-64-1 | 12<br>8 | 13<br>9 | —<br>— | Cat 2 | Cat 2A |
| 7 | Lactic acid | 50-21-5 | 13<br>11 | 14<br>11 | —<br>— | Cat 1 | Cat 1 |
| 8 | Chlorhexidine | 55-56-1 | 13<br>12 | 14<br>11 | —<br>— | Cat 1 | Cat 1 |
| 9 | Benzalkonium chloride 5% | 8001-54-5 | 14<br>12 | 17<br>11 | —<br>— | Cat 1 | Cat 1 |
| 10 | Hexadecyltrimethylammonium bromide 6% | 57-09-0 | 13<br>12 | 15<br>13 | —<br>— | Cat 1 | Cat 1 |
| 11 | Triton X-100 10% | 9002-93-1 | 16<br>11 | 17<br>12 | —<br>— | Cat 1 | Cat 1 |
| 12 | Benzethonium chloride 10% | 121-54-0 | 12<br>12 | 14<br>12 | —<br>— | Cat 1 | Cat 1 |
| 13 | Methyl thioglycolate | 2365-48-2 | 16<br>15 | 17<br>14 | —<br>— | Cat 1 | Cat 1 |
| 14 | Diethylaminopropionitrile | 5351-04-2 | 15<br>15 | 14<br>12 | —<br>— | Cat 1 | Cat 1 |
| 15 | Tetraethylene glycol diacrylate | 17831-71-9 | 11<br>7 | 11<br>4 | —<br>— | Cat 2 | Cat 1 |
| 16 | 1-Chloroctan-8-ol | 23144-52-7 | 17<br>13 | 15<br>11 | —<br>— | Cat 1 | Cat 1 |
| 17 | [3-(2-Aminoethylamino)propyl]trimethoxysilane | 1760-24-3 | 12<br>15 | 16<br>14 | —<br>— | Cat 1 | cat 1 |
| 18 | Sodium hydroxide 0.3% | 1310-73-2 | 12<br>5 | 17<br>3 | —<br>— | Cat 2 | Cat 2A |
| 19 | 2,6-Dichlorobenzoyl chloride | 4659-45-4 | 17<br>8 | 15<br>8 | —<br>— | Cat 2 | Cat 2A |
| 20 | Gamma-butyrolactone | 96-48-0 | 17<br>8 | 16<br>8 | —<br>— | Cat 2 | Cat 2A |
| 21 | Allyl alcohol | 107-18-6 | 17<br>8 | 15<br>7 | —<br>— | Cat 2 | Cat 2A |
| 22 | Chlorhexidine gluconate (20%) | 18472-51-0 | 12<br>5 | 13<br>5 | —<br>— | Cat 2 | Cat 2A |
| 23 | Propasol Solvent P | 1569-01-3 | 15<br>16 | 17<br>17 | —<br>— | Cat 1 | Cat 2A |
| 24 | 2-Methyl-1-pentanol | 105-30-6 | 15<br>8 | 15<br>6 | —<br>— | Cat 2 | Cat 2B |
| 25 | iso-Butanal | 78-84-2 | 15<br>6 | 20<br>8 | —<br>— | Cat 2 | Cat 2B |
| 26 | 3-Chloropropionitrile | 542-76-7 | 16<br>8 | 11<br>7 | —<br>— | Cat 2 | Cat 2B |
| 27 | Ethyl-2-methylacetoacetate | 609-14-3 | 12<br>6 | 9<br>8 | 13<br>7 | Cat 2* | Cat 2B |
| 28 | Glycolic acid (10%) | 79-14-1 | 17<br>8 | 13<br>9 | —<br>— | Cat 2 | Cat 2B |
| 29 | Diethyl toluamide | 134-62-3 | 17<br>9 | 17<br>8 | —<br>— | Cat 2 | Cat 2B |
| 30 | Glycerol | 56-81-5 | 0<br>0 | 0<br>0 | —<br>— | No Cat | No Cat |
| 31 | Tween 20 | 9005-64-5 | 2<br>0 | 0<br>0 | —<br>— | No Cat | No Cat |
| 32 | Octyltrimethoxysilane (SILAN 108) | 3069-40-7 | 6<br>0 | 10<br>3 | 8<br>2 | No Cat* | No Cat |
| 33 | 1,9-Decadiene | 1647-16-1 | 7<br>0 | 4<br>0 | —<br>— | No Cat | No Cat |
| 34 | 2,4-Pentanediol | 625-69-4 | 9<br>6 | 7<br>2 | —<br>— | No Cat | No Cat |
| 35 | 2-Ethoxyethyl methacrylate | 2370-63-0 | 9<br>4 | 7<br>3 | —<br>— | No Cat | No Cat |
| 36 | Dipropyl disulfide | 629-19-6 | 7<br>6 | 5<br>4 | —<br>— | No Cat | No Cat |
| 37 | n-Hexyl bromide | 111-25-1 | 8<br>6 | 10<br>4 | 6<br>3 | No Cat* | No Cat |

TABLE 3-continued

Results of the analysis of the 39 liquid products tested by the eye irritation test (EIT) and comparison with the results obtained by the Draize test

| No | Chemical | CAS RN | Irritation INDEX | 100% 30% | EIT prediction | UN-GHS |
|---|---|---|---|---|---|---|
| 38 | Polyoxyethylene hydrogenated castor oil (Kolliphor) | 61788-85-0 | 7 4 | 4 0 | — — | No Cat | No Cat |
| 39 | 1-Ethyl-3-methylimidazolium ethylsulfate | 342573-75-5 | 9 10 5 5 | 5 3 | No Cat* | No Cat |

TABLE 4

Measurement of the predictive ability of the eye irritation test to differentiate between eye irritants (classified as Cat 1 or Cat 2) and non-irritants (no Cat) on a set of 39 chemicals

| DRAIZE | Classified | No Category |
|---|---|---|
| Classified (n) | 27 | 0 |
| No Category (n) | 0 | 12 |
| Total (n) | 27 | 12 |
| Sensitivity (%) | 100 | |
| Specificity (%) | 100 | |
| Accuracy (%) | 100 | |

TABLE 5

Confusion matrix analysis of the predictive ability of the eye irritation test to separate into 3 irritation classes (Cat 1, Cat 2 and no Cat) according to UN-GHS recommendations.

| | | Eye irritation test | | | Classification Overall | Producer accuracy (Accuracy) |
|---|---|---|---|---|---|---|
| | | Cat 1 | Cat 2 | No Cat | | |
| UNGHS | Cat 1 | 11 | 1 | | 12 | 91.66% |
| | Cat 2 | 1 | 14 | | 15 | 93.33% |
| | No Cat | | | 12 | 12 | 100% |
| | Truth Overall | 12 | 15 | 12 | 39 | |
| | User accuracy (Recall) | 91.66% | 93.33% | 100% | | |
| Overall Accuracy | | 95% | | | | |
| Kappa | | 0.923 | | | | |

TABLE 6

List of solid chemicals studied

| CAS Number | CHEMICAL Name | GHS Class |
|---|---|---|
| 594-61-6 | alpha-Hydroxyisobutyric acid [2-Hydroxyisobutyric acid] | Cat 1 |
| 58-33-3 | Promethazine hydrochloride | Cat 1 |
| 79-92-5 | Camphene | Cat 2B |
| 62-76-0 | Sodium oxalate | Cat 1 |
| 110-03-2 | 2,5-Dimethylhexanediol | Cat 1 |
| 86-87-3 | 1-Naphthalene acetic acid | Cat 1 |
| 83-56-7 | 1,5-Naphthalenediol INCI name: 1,5-NAPHTHALENEDIOL | Cat 2A |
| 101-20-2 | 1-(4-Chlorophenyl)-3-(3,4-dichlorophenyl) urea INCI name: TRICLOCARBAN | No cat |
| 103597-45-1 | 2,2'-Methylene-bis-(6-(2H-benzotriazol-2-yl)-4-(1,1,3,3-tetramethylbutyl)phenol) INCI name: METHYLENE BIS-BENZOTRIAZOLYL TETRAMETHYLBUTYLPHENOL | No cat |
| 53112-28-0 | 2-Anilino-4,6-dimethylpyrimidine common name: Pyrimethanil | No cat |
| 3234-85-3 | Tetradecyl tetradecanoate INCI name: Myristyl myristate | No cat |
| 118-82-1 | 4,4'-Methylene bis-(2,6-di-tert-butylphenol) | No cat |
| 589-10-6 | 4-Bromophenetol | No cat |
| 14075-53-7 | Potassium tetrafluoroborate | No cat |
| 21645-51-2 | Aluminum hydroxide | No cat |

TABLE 7

Results of the analysis of the 15 solid products tested by the eye irritation test (EIT) and comparison with the results obtained by the Draize test

| No | Chemical name | CAS RN | Irritation INDEX | | | EIT prediction | UN-GHS |
|---|---|---|---|---|---|---|---|
| 1 | 2-Hydroxyisobutyric acid | 594-61-6 | 34 | 28 | 32 | Cat 1 | Cat 1 |
| 2 | Promethazine hydrochloride | 58-33-3 | 34 | 32 | 30 | Cat 1 | Cat 1 |
| 3 | Camphene | 79-92-5 | 10 | 12 | 13 | Cat 2 | Cat 2B |
| 4 | Sodium oxalate | 62-76-0 | 22 | 24 | 32 | Cat 1 | Cat 1 |
| 5 | 2,5-Dimethylhexanediol | 110-03-2 | 22 | 23 | 21 | Cat 1 | Cat 1 |
| 6 | 1-Naphthalene acetic acid | 86-87-3 | 26 | 28 | 25 | Cat 1 | Cat 1 |
| 7 | 1,5-Naphthalenediol | 83-56-7 | 12 | 18 | 15 | Cat 2 | Cat 2A |
| 8 | Triclocarban | 101-20-2 | 0 | 0 | 1 | No Cat | No Cat |
| 9 | Methylene bis-benzotriazolyl tetramethylbutyl phenol | 103597-45-1 | 2 | 4 | 3 | No Cat | No Cat |
| 10 | Pyrimethanil | 53112-28-0 | 0 | 0 | 0 | No Cat | No Cat |
| 11 | Myristyl myristate | 3234-85-3 | 2 | 3 | 1 | No Cat | No Cat |
| 12 | 4,4'-Methylene bis-(2,6-di-tert-butylphenol) | 118-82-1 | 3 | 0 | 0 | No Cat | No Cat |

TABLE 7-continued

Results of the analysis of the 15 solid products tested by the eye irritation test (EIT) and comparison with the results obtained by the Draize test

| No | Chemical name | CAS RN | Irritation INDEX | EIT predic-tion | UN-GHS |
|----|---------------|--------|------------------|-----------------|--------|
| 13 | 4-Bromophenetol | 589-10-6 | 2 | 2 | 3 | No Cat | No Cat |
| 14 | Potassium tetrafluoroborate | 14075-53-7 | 4 | 6 | 2 | No Cat | No Cat |
| 15 | Aluminum hydroxide | 21645-51-2 | 0 | 0 | 0 | No Cat | No Cat |

TABLE 8

Measurement of the predictive ability of the eye irritation test to differentiate between eye irritants (classified as Cat 1 or Cat 2) and non-irritants (no Cat) on a set of 15 solid chemicals

| DRAIZE | Classified | No Category |
|--------|-----------|-------------|
| Classified (n) | 7 | 0 |
| No Category (n) | 0 | 8 |
| Total (n) | 7 | 8 |
| Sensitivity (%) | | 100 |
| Specificity (%) | | 100 |
| Accuracy (%) | | 100 |

TABLE 9

Confusion matrix analysis of the predictive ability of the eye irritation test to separate into 3 irritation classes (Cat 1, Cat 2 and no Cat) according to UN-GHS recommendations for the 15 solid products.

| | | Eye irritation test | | | | "Producer accuracy" (Accuracy) |
|---|---|---|---|---|---|---|
| | | Cat 1 | Cat 2 | No Cat | Classification | |
| UNGHS | Cat 1 | 5 | | | 5 | 100% |
| | Cat 2 | | 2 | | 2 | 100% |
| | No Cat | | | 8 | 8 | 100% |
| | "Truth Overall" | 5 | 2 | 8 | 15 | |
| | "User accuracy" (Recall) | 100% | 100% | 100% | | |
| "Overall Accuracy" | | 100% | | | | |
| Kappa | | 1 | | | | |

The invention claimed is:

1. A method for evaluating the eye irritation potential of a test compound, comprising the steps of:
   a) bringing a test compound into contact with an in vitro reconstructed corneal sample;
   b) measuring the expression of at least 10 genes selected from the group consisting of: HSP90AA1, COL7A1, NOS3, MMP8, CASP1, ELN, IL-23R, DLK1, CLEC4D, IL-24, CCL22, SLIT2, ICAM2, MUC13, HSPA1A, FSHR, IL-1R2, ALB, CCND1, CXCL1, CXCR1, KL, COL6A2, MUC4, DDIT3, MMP3, HAS1, IRF1 and CYR61, wherein at least two of the genes are DLK1 and IL-1R2;
   c) comparing the expression of each measured gene in the in vitro reconstructed corneal sample to a control sample in which the expression of said measured gene in the absence of said test compound is measured;
   d) measuring an overexpression of the genes measured in step b) wherein an overexpression threshold value is assigned to each gene measured in step b), wherein the overexpression threshold value corresponds to a factor of increase in the expression of the gene when the in vitro reconstructed corneal sample is brought into contact with the test compound relative to the expression of said gene the control sample, and wherein an eye irritation index of the test compound corresponds to the overexpression threshold value,
   e) categorizing the test compound as not irritant, reversible irritant, or irreversible irritant based on the eye irritation index of the test compound wherein when the test compound is brought into contact with the in vitro reconstructed corneal sample in a solid form at 60 mg/cm$^2$, if the eye irritation index of the test compound is greater than or equal to 20, the test compound is an irreversible irritant, if the eye irritation index of the test compound is greater than or equal to 10 and less than 20 the test compound is a reversible irritant, and if the eye irritation index of the test compound is less than 10 the test compound is not an irritant, and
   f) including the test compound in a pharmaceutic or cosmetic if the test compound is categorized as not irritant or reversible irritant and excluding the test compound in a pharmaceutic or cosmetic if the test compound is categorized as irreversible irritant.

2. The method according to claim 1, wherein the bringing into contact of the test compound in step a) is carried out with the test compound in solid form and wherein step b) comprises measuring the expression of at least 10 of the following genes: IL-24, IL-23R, DDIT3, MMP8, DLK1, HAS1, CYR61, IL1R2, CLEC4D, ICAM2, CASP1, MUC13 and MUC4.

3. The method according to claim 1, wherein the bringing into contact of the test compound in step a) is carried out with the test compound in liquid form and wherein step b) comprises measuring the expression of at least the following 10 genes: HSP90AA1, CASP1, DLK1, CLEC4D, IL-24, SLIT2, HSPA1A, FSHR, IL-1R2 and CCND1.

4. The method according to claim 1, wherein the in vitro reconstructed corneal sample is a sample comprising immortalized corneal epithelial cells, grown in defined culture medium and arranged in a thin layer on a synthetic membrane at the water-air interface.

* * * * *